(12) United States Patent
Sevick-Muraca et al.

(10) Patent No.: US 6,771,370 B2
(45) Date of Patent: Aug. 3, 2004

(54) CHARACTERIZING POWDERS USING FREQUENCY-DOMAIN PHOTON MIGRATION

(75) Inventors: Eva M. Sevick-Muraca, College Station, TX (US); Zhigang Sun, Houston, TX (US); Tianshu Pan, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 10/274,790

(22) Filed: Oct. 21, 2002

(65) Prior Publication Data

US 2003/0117622 A1 Jun. 26, 2003

Related U.S. Application Data

(60) Provisional application No. 60/339,121, filed on Oct. 22, 2001.

(51) Int. Cl.[7] .............................................. G01N 21/51
(52) U.S. Cl. ...................................... 356/336; 356/342
(58) Field of Search ................................ 356/335, 336, 356/342

(56) References Cited

U.S. PATENT DOCUMENTS

| | | | | |
|---|---|---|---|---|
| 5,424,843 A | * | 6/1995 | Tromberg et al. | 356/442 |
| 5,818,583 A | * | 10/1998 | Sevick-Muraca et al. | 356/336 |
| 6,480,276 B1 | * | 11/2002 | Jiang | 356/336 |

FOREIGN PATENT DOCUMENTS

| | | | | |
|---|---|---|---|---|
| WO | WO 99/49312 | | 3/1999 | G01N/33/15 |
| WO | WO 01/22063 A1 | | 9/2000 | G01N/21/35 |

OTHER PUBLICATIONS

Gratton, et al., *A Continuously Variable Frequency Cross-Correlation Phase Fluorometer with Picosecond Resolution*, © Biophysical Society, Biophysical Journal, vol. 44, pp. 315–324, Dec. 1983.

Gratton, et al., *The possibility of a near–infrared optical imaging system using frequency domain methods*, Mind Brain Imaging Program, Hamamatsu, Japan, pp. 183–189, Aug. 5–10, 1990.

Sevick, et al., *Quantitation of Time–and Frequency–Resolved Optical Spectra for the Determination of Tissue Oxygenation*, Analytical Biochemistry 195, © 1991 Academic Press Inc., pp. 330–351, 1991.

(List continued on next page.)

*Primary Examiner*—Frank G. Font
*Assistant Examiner*—Layla Lauchman
(74) *Attorney, Agent, or Firm*—Baker Botts L.L.P.

(57) ABSTRACT

Characterizing a powder bed includes generating measurements by repeating the following. A location of the powder bed is illuminated with light having a time varying intensity with a resolution of less than one hundred nanoseconds. The particles scatter the light to alter the time varying intensity. The light propagates through a portion of the particles that defines a sampled volume. The light received from the powder bed is detected. The altered time-varying intensity of the light is measured to generate a time-dependent signal having a time-dependence that is less than or equal to a time-of-flight of a photon of the propagating light. An optical property is determined from the time-dependent signal, and a characteristic is determined from the optical property. The sampled volume is determined, and variance of the measurements is calculated. Uniformity of the powder bed is determined in accordance with the variance and the sampled volume.

32 Claims, 9 Drawing Sheets

OTHER PUBLICATIONS

Fishkin, et al., *Propagation of photon–density waves in strongly scattering media containing an absorbing semi–infinite plane bounded by a straight edge*, vol. 10, No. 1, © 1993 Optical Society of America, pp. 127–140, Jan. 1993.

Tromberg, et al., *Properties of photon density waves in multiple–scattering media*, vol. 32, No. 4, Applied Optics, pp. 607–616, Feb. 1, 1993.

Madsen, et al., *Determination of the optical properties of the human uterus using frequency–domain photon migration and steady–state techniques*, Phys. Med. Biol. 39, © 1994 IOP Publishing Ltd., pp. 1191–1202, 1994.

Fantini, et al., *Quantitative determination of the absorption spectra of chromophores in strongly scattering media: a light–emitting–diode based technique*, Applied Optics, vol. 33, No. 22, pp. 5204–5213, Aug. 1, 1994.

Fishkin, et al., *Frequency–domain method for measuring spectral properties in multiple–scattering media: methemoglobin absorption spectrum in a tissuelike phantom*, Applied Optics, vol. 34, No. 7, pp. 1143–1155, Mar. 1, 1995.

Tromberg, et al., *Non–invasive measurements of breast tissue optical properties using frequency–domain photon migration*, Phil. Trans. R. Soc. Lond. B, © 1997 The Royal Society, pp. 661–668, 1997.

Muzzio, et al., *Sampling practices in powder blending*, Research papers, International Journal of Pharmaceutics 155, © 1997 Elsevier Science B.V., pp. 153–178, 1997.

Fishkin, et al., *Frequency–domain photon migration measurements of normal and malignant tissue optical properties in a human subject*, Applied Optics, vol. 36, No. 1, pp. 10–20, Jan. 1, 1997.

Sevick–Muraca, et al., *Photon–Migration Measurement of Latex Size Distribution in Concentrated Suspensions*, Particle Technology and Fluidization, AIChE Journal, vol. 43, No. 3, pp. 655–664, Mar. 1997.

Richter, et al., *Particle Sizing Using Frequency Domain Photon Migration*, Part. Part. Syst. Charact. 15, © WILEY–VCH Verlag GmbH, D–69469 Weinheim, pp. 9–15, 1998.

Ramanujam, et al., *Sources of phase noise in homodyne and heterodyne phase modulation devices used for tissue oximetry studies*, Review of Scientific Instruments, vol. 69, No. 8, © 1998 American Institute of Physics, pp. 3042–3054, Aug. 1998.

Chance, et al., Review Article, *Phase measurement of light absorption and scatter in human tissue*, Review of Scientific Instruments, vol. 69, No. 10, © 1998 American Institute of Physics, pp. 3457–3481, Oct. 1998.

Banerjee, et al., *Probing Static Structure of Colloid–Polymer Suspensions with Multiply Scattered Light*, Journal of Colloid and Interface Science 209, © 1999 by Academic Press, pp. 142–153, 1999.

Shinde, et al., *Investigation of static structure factor in dense suspensions by use of multiply scattered light*, Applied Optics, vol. 38, No. 1, © 1999 Optical Society of America, pp. 197–204, Jan. 1. 1999.

Gerken, et al., *High–precision frequency–domain measurements of the optical properties of turbid media*, Optics Letters, vol. 24, No. 14, © 1999 Optical Society of America, pp. 930–932, Jul. 15, 1999.

Shinde, et al., *Frequency–Domain Photon Migration Measurements for Quantitative Assessment of Powder Absorbance: A Novel Sensor of Blend Homogeneity*, Research Articles, © 1999 American Chemical Society and American Pharmaceutical Association, Journal of Pharmaceutical Sciences, vol. 88, No. 10, pp. 959–966, Oct. 1999.

Banerjee, et al., *Assessment, of S(0, Ø) from multiply scattered light*, Journal of Chemical Physics, vol. 111, No. 20, © 1999 American Institute of Physics, pp. 9133–9136, Nov. 22, 1999.

Richter, et al., *Characterization of concentrated colloidal suspensions using time–dependent photon migration measurements*, Reprinted from Colloids And Surfaces An International Journal, A: Physicochemical and Engineering Aspects, © 2000 Elsevier Science B.V., pp. 163–173, plus cover, 2000.

Pham, et al., *Broad bandwidth frequency domain instrument for quantitative tissue optical spectroscopy*, Review of Scientific Instruments, vol. 71, No. 6, © 2000 American Institute of Physics, pp. 2500–2513, Jun. 2000.

Hawrysz, et al., *Developments Toward Diagnostic Breast Cancer Imaging Using Near–Infrared Optical Measurements and Fluorescent Contrast Agents*[1], Review Article, Neoplasia, vol. 2, No. 5, © 2000 Nature America, Inc., pp. 388–417, Sep.–Oct., 2000.

Pan, et al., *Volume of Pharmaceutical Powders Probed by Frequency–Domain Photon Migration Measurements of Multiply Scattered Light*, Analytical Chemistry 2002, vol. 74, No. 16, © 2002 American Chemical Society, pp. 4228–4234, Aug. 15, 2002.

\* cited by examiner

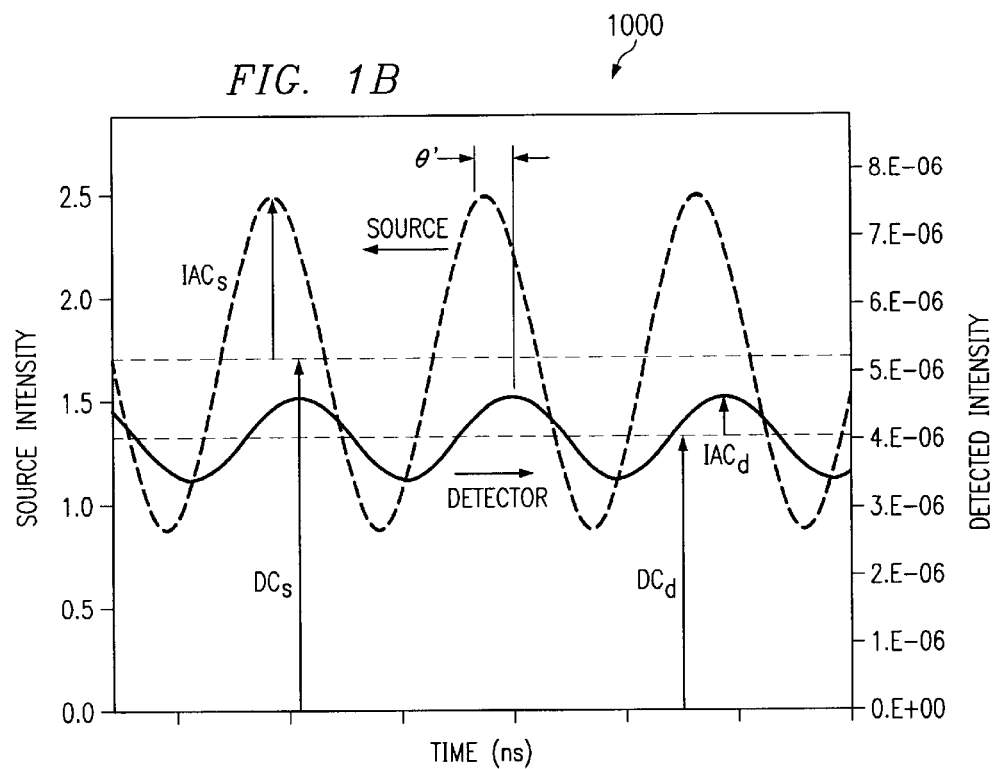
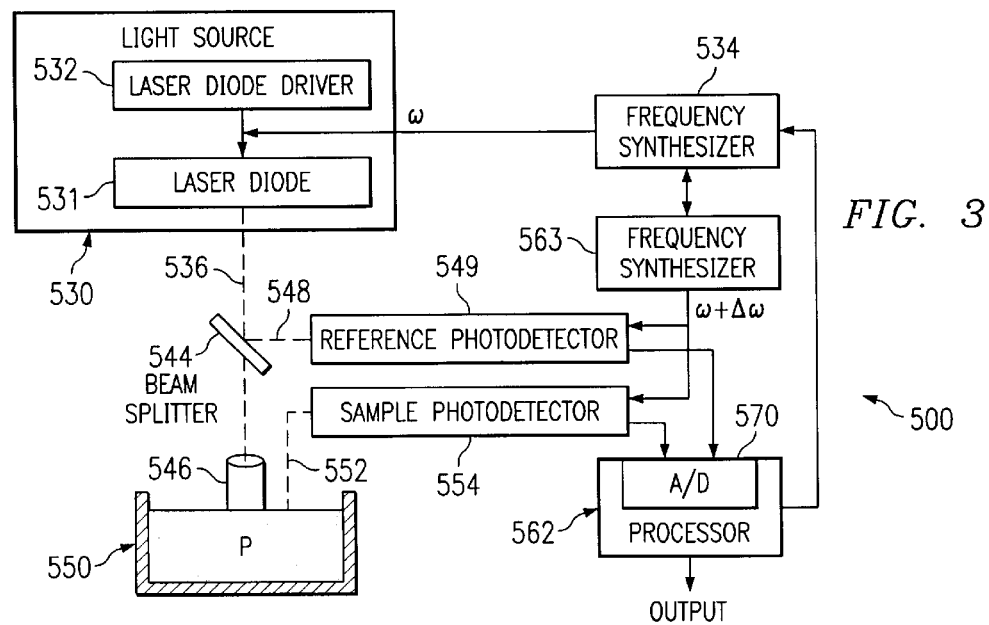

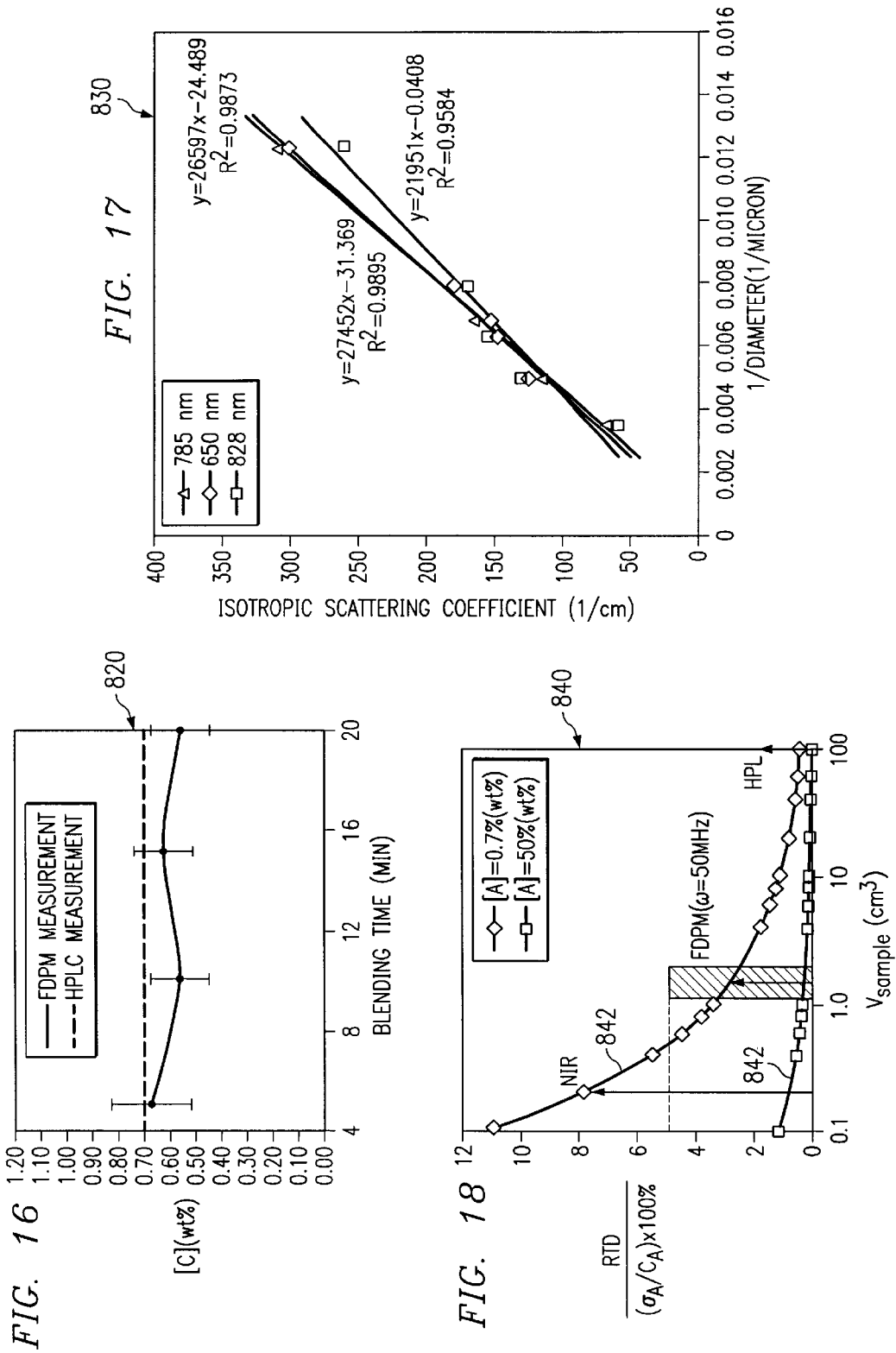

CHARACTERIZING POWDERS USING FREQUENCY-DOMAIN PHOTON MIGRATION

RELATED APPLICATION

This application claims benefit under 35 U.S.C. §119(e) of U.S. Provisional Application Serial No. 60/339,121, entitled "APPARATUS AND METHOD FOR ASSESSING POWDER CHARACTERISTICS," filed Oct. 22, 2001.

GOVERNMENT FUNDING

The U.S. Government may have certain rights in this invention as provided for by the terms of Grant No. CTS-9876583 awarded by the National Science Foundation and Grant No. 1K04 CA68374-01 awarded by the National Institutes of Health.

TECHNICAL FIELD OF THE INVENTION

This invention relates generally to the field of powder characterization and more specifically to characterizing powders within powder beds using frequency-domain photon migration.

BACKGROUND OF THE INVENTION

Accurate measurement of the characteristics of a powder bed such as the particle size or content uniformity of the powder bed are important in a number of areas. In the pharmaceutical and chemical industries, powder blending is often required to be accomplished properly to ensure product quality. For example, in the pharmaceutical industry, powder blend uniformity prior to tableting must be monitored to ensure the proper dosage of each tablet. Powder blending involves compression of an excipient material with an active ingredient. The blending of the excipient material and the smaller amount of the active ingredient is typically accomplished by rotating and vibrating blenders.

Particle segregation may occur based on differences in the size, density, charge, and/or shape of the particles. Particle segregation may result from over-blending, and may occur while transferring the powder between containers or while storing the powder. More importantly, the non-uniformity of a powder bed may result in segregation of an active ingredient. The uniformity of a powder bed, however, may be difficult to assess since both the excipient material and active ingredient are typically white powders.

Validation of blending operations and monitoring of blend uniformity in the pharmaceutical industry are regulated by the U.S. Food and Drug Administration, which requires measurements involving a validation study to assure future blending operations will provide a consistent blend. Yet, there are few methods for validation of blend uniformity with sampling and measurement errors within the tolerances set by the U.S. Food and Drug Administration. Continuous monitoring of blend uniformity within the blending and tableting processes could eliminate the need for validation studies, and would provide economical quality assurance of the operations. Evaluation of the uniformity of stored powder blends can ensure feedstock quality in many types of powder processing operations in the pharmaceutical, bulk, and specialty chemical industries.

One technique for assessing blend uniformity uses near-infrared spectroscopy (NIRS) to assess blend homogeneity from a differential absorbance spectrum of active ingredients. A sample is exposed to near-infrared light, and emitted attenuated light from the sample is detected. (See PCT Patent Application, Publication No. WO 01/22063 A1, entitled "Method and Apparatus for Spectrometric Analysis of Turbid, Pharmaceutical Samples," to Folestad, Josefson, Johansson.)

Laser induced fluorescence (LIF) measures weak fluorescence emissions originating from an active ingredient when excited by ultra-violet (UV) light. One drawback to the LIF technique is that it requires an optical window in a rotating blender and a synchronized light source and detector. Others drawbacks are that the effects of changing particle size can mask the fluorescence signals that could indicate blend content non-uniformity, and that there are many agents that do not provide a fluorescent signal.

The techniques of NIRS and LIF suffer from disadvantages. For example, the attenuation of light may be affected by changes in the absorption and scattering properties of a powder, but the NIR and LIF techniques cannot discriminate between changes in the absorption and scattering properties that are due to the presence of the active ingredient or to the size of the inert powder particles, respectively. Accordingly, the precision of measurements of uniformity may be insufficient.

In addition, the NIRS and LIF techniques interrogate a small volume of powder, which increases the variance of the measurement (See Muzzio, F. J.; Robinson, P.; Wightman, C.; Brone D. *International Journal Pharmaceutics.* 1997, 155, 153–178.) The complete random mixture model provides a theoretical prediction of the lowest possible measurement variance of a two component powder, as described by Equation (1):

$$\sigma^2 = \frac{W_A(1-W_A)}{N} \cdot \frac{\rho_2}{\rho_1} \qquad (1)$$

where $W_A$ is the weight percent of an active ingredient A, N is the number of particles of sample, $\rho_1$ is the density of active ingredients A, and $\rho_2$ is the density of the excipient material. For an optical probe, N is the ratio of sampled volume to mean single particle volume, as defined by Equation (2):

$$N = \frac{V_{sample}}{V_{particle}}. \qquad (2)$$

According to Equation (1), for a low dose concentration, if the weight percent of active ingredient A is small, and if the sampled volume is small, the minimum variance is larger than for a higher dose concentration and a larger sampled volume. Since the NIR spectroscopy and LIF techniques can interrogate only relatively small samples, they may not provide satisfactory measurements for some low dose concentrations. Consequently, determining the characteristics of a powder has posed difficulties, especially in the pharmaceutical industry where powder bed uniformity is crucial and must be controlled.

SUMMARY OF THE INVENTION

In accordance with the present invention, disadvantages and problems associated with previous techniques for characterizing powder beds may be reduced or eliminated.

Characterizing a powder bed includes generating measurements by repeating the following. A location of the powder bed is illuminated with light having a time varying intensity with a resolution of less than one hundred nanoseconds. The particles scatter the light to alter the time varying intensity. The light propagates through a portion of the particles that defines a sampled volume. The light received from the powder bed is detected. The altered time-varying intensity of the light is measured to generate a time-dependent signal having a time-dependence that is less than or equal to a time-of-flight of a photon of the propagating light. An optical property is determined from the time-dependent signal, and a characteristic is determined from the optical property. The sampled volume is determined, and variance of the measurements is calculated. Uniformity of the powder bed is determined in accordance with the variance and the sampled volume.

Certain embodiments of the invention may provide one or more technical advantages. For example, according to one embodiment, a frequency-domain photon migration (FDPM) technique is used to obtain measurements of separate absorption and scattering properties of a powder bed. The measurements may be used to determine one or more characteristics of a powder bed, for example, the sizes of the particles of the powder bed, the concentration of an active agent, or the volume of powder being sampled. The measurements may be used to track changes of a characteristic of a powder bed undergoing blending, mixing, transfer, or storage.

Another technical advantage of one embodiment may be that an absorption coefficient and an isotropic scattering coefficient for a powder are obtained as separate parameters rather than a single product. The separate parameters allow for estimation of distinct characteristics describing of the powder bed uniformity, which may be used to detect downstream segregation effects and assess excipient uniformity.

Yet another technical advantage of one embodiment may be that larger volumes of powders, such as one to three times dosage weight as recommended by the Food and Drug Administration Good Manufacturing Practice guidelines, may be sampled. The larger sampled volumes, as compared to those of the NIRS and LIF techniques, yields a smaller natural variance for FDPM measurements. The smaller variance allows for a more precise assessment of blend uniformity, and enables evaluation of the uniformity of low dose powder blends. Accordingly, unlike other approaches, the embodiment may provide accurate measurement of low dosage formulations due to the separate determination of absorption and scattering properties and to the sampling of larger volumes.

Yet another technical advantage of one embodiment may be that a handheld or an in situ probe may be used to determine characteristics of a powder. A handheld probe may also be readily inserted into the powder, and an in situ probe may be used within a rotating or tumbling powder blender to provide convenient characterization of the powder. A probe may include circuits for miniaturization such as a chip sensor. Yet another technical advantage of one embodiment may be that the FDPM technique is self-calibrating. Yet another technical advantage of one embodiment may be that the measurements may be multiplexed using laser diode or light emitting diodes of various wavelengths. Yet another technical advantage of one embodiment may be that the technique does not require sampling or extraction of powder samples, reducing the increased variance owing to sampling practices.

Certain embodiments of the invention may include none, some, or all of the above technical advantages. One or more other technical advantages may be readily apparent to one skilled in the art from the figures, descriptions, and claims included herein.

BRIEF DESCRIPTION OF THE DRAWINGS

For a more complete understanding of the present invention and its features and advantages, reference is now made to the following description, taken in conjunction with the accompanying drawings, in which:

FIG. 1B is a diagram illustrating frequency-domain photon migration;

FIG. 3 is a block diagram illustrating one embodiment of another system for determining characteristics of a powder bed;

FIG. 16 is a diagram illustrating example measurements of active pharmaceutical ingredient concentrations;

FIG. 17 is a diagram illustrating example measurements of particle size; and

FIG. 18 is a diagram illustrating example relative standard deviations of concentration versus sampled volumes.

DETAILED DESCRIPTION OF THE DRAWINGS

Embodiments of the present invention and its advantages are best understood by referring to FIGS. 1A through 18 of the drawings, like numerals being used for like and corresponding parts of the various drawings.

Figure 1A:
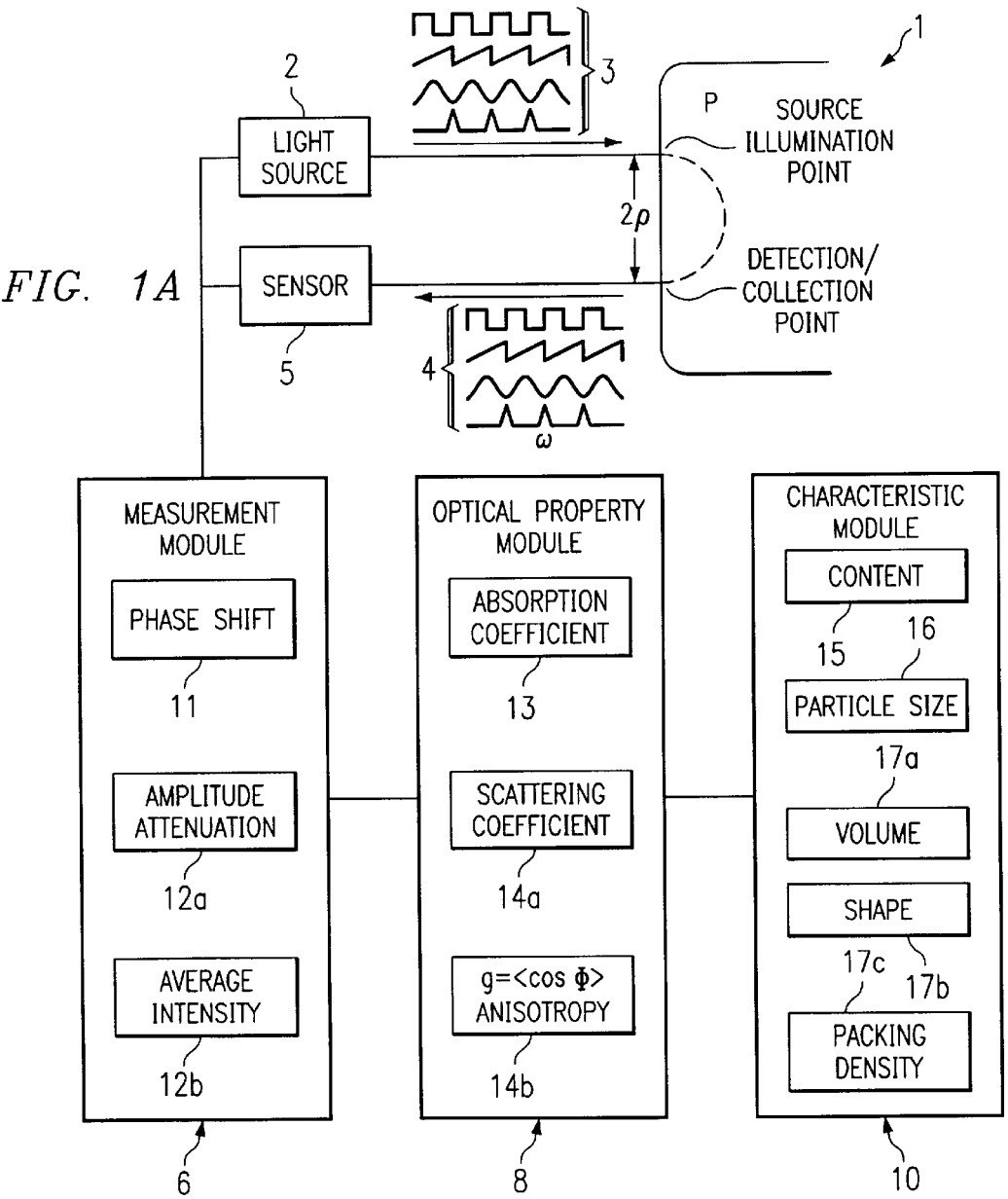
FIG. 1A is a block diagram illustrating one embodiment of a system for determining characteristics of a powder bed.

FIG. 1A is a block diagram illustrating one embodiment of a system 1 for determining characteristics of a powder bed P. In general, system 1 uses measurements of photon time-of-flight such as frequency-domain photon migration measurements to determine characteristics of a powder bed. Characteristics may include, for example, the concentration of ingredients, uniformity of content ingredients, particle size, uniformity of particle size, and volume of sampled powder. Frequency-domain photon migration measurements, an example of measurements of time-dependent light propagation, or photon time-of-flight, is described with reference to FIG. 1B.

FIG. 1B is a diagram 1000 illustrating frequency-domain photon migration. Intensity modulated, monochromatic or polychromatic light at modulation frequencies ranging from hundreds of kilohertz to hundreds of megahertz is introduced into the powder bed. As light propagates through the powder bed, the amplitude of the light is attenuated by an attenuation factor $I_{AC}$ relative to the incident light, and the phase of the light is phase-delayed by a phase shift θ'. Measurements of phase shift θ' and attenuation factor $I_{AC}$ are acquired at different modulation frequencies ω, wavelengths λ, and/or distances 2ρ from the point of incident illumination. Optical properties such as an absorption coefficient $\mu_a$, powder anisotropy g, and scattering coefficient $\mu_s$ are computed from phase shift θ', amplitude attenuation $I_{ACd}$, and average intensity of the signal $DC_d$ from a mathematical model that may comprise a diffusion approximation or approximation to a radiative transport equation. Characteristics of the powder bed may be determined from the optical properties.

Referring back to FIG. 1A, a light source 2 directs incident light 3 towards a powder bed P. Powder bed P may comprise a pharmaceutical powder or other suitable powder such as powders used for foodstocks, pigments, or agricultural fertilizers. The powder may be in motion, as in a transfer duct, rotating powder blender or mixer, or within a stationary container. Incident light 3 may comprise light with a time-varying intensity such as pulsed light with femtosecond to nanosecond full-width half maximum pulses or intensity modulated waveform light with a square wave, sine wave, or other suitable waveform. According to one embodiment, incident light 3 may be intensity modulated at radio frequencies such as hundreds of kilohertz to hundreds of megahertz. Incident light 3 may be delivered as a point of incident light via a fiber optic or as an expanded beam. The particles within powder bed P interact with and scatter incident light 3, yielding time-varying scattered light 4 that differs from incident light 3.

Sensor 5 detects scattered light 4. Sensor 5 may comprise, for example, a fast electro-optical detector and/or mixed signal detection system that is sufficiently fast, such as on the order of femtosecond to nanosecond, or smaller time-scale, resolution, to preserve and record changes in the pulse shape or waveform. Scattered light 4 may be collected in any suitable manner, such as at a point via a fiber optic or across an area via optics. Scattered light 4 is typically intensity modulated at approximately the same frequency as incident light 3 and is collected from a point a distance 2ρ away from the incident source and directed to sensor 4. The modulated intensity of scattered light, however, may be phase shifted relative to incident light 3. A phase shift module 11 of measurement module 6 measures the phase shift of scattered light 4. The amplitude of scattered light 4 may be attenuated relative to incident light 3. An amplitude attenuation module 12 of measurement module 6 measures the amplitude attenuation of scattered light 4. The average intensity of the modulated signal module 12b of measurement module 6 measures the average intensity $DC_d$ of the modulated signal.

Optical property module 8 determines optical properties of powder bed P according to the phase shift, amplitude attenuation, and average intensity of the modulated signal using a model of light propagation within the powder. Optical properties may include an absorption coefficient, powder anisotropy, and scattering coefficient. An absorption coefficient module 13 determines the absorption coefficient, a scattering coefficient module 14a determines the scattering coefficient, and a scattering anisotropy module 14b determines the mean cosine of scattering from the powder.

A characteristic module 10 determines characteristics of powder bed P in accordance with the optical property. Characteristics may include, for example, the concentration of ingredients, uniformity of content ingredients, particle size, uniformity of particle size, and volume of sampled powder. Other characteristics may include particle shape, volume fraction, or packing density of the powder. A content module 15 determines the concentration of the ingredients of particle blend P and the uniformity of the ingredients. A particle size module 16 determines the particle size and uniformity of particle size, and a volume module 17a determines the volume of sampled powder. A shape module 17b provides a characteristic that describes the shape of the particles, and a packing density module 17c provides a characteristic that describes the volume fraction of powder particles or the packing density.

System 1 provides for measurement of the local uniformity of powder bed P and changes of the local uniformity during powder blending, which may provide for a process measurement to validate the blending process. Typically, the variance of a powder characteristic such as active pharmaceutical ingredient (API) content is used to assess blend content uniformity for regulatory purposes, so the measurement of the characteristic may be required to have a smaller measurement variance in order to determine whether the criteria for blend content uniformity has been met. In contrast to other techniques such as near infrared spectroscopy (NIRS) and laser induced fluorescence (LIF), system 10 involves the propagation of light through a significant volume of the powders, which may reduce the variance of the measurements.

Examples of system 10 showing how scattered light 4 emitted from a powder bed P can be measured are described in more detail with reference to FIGS. 3 and 8. Any other suitable implementation may be used. For example, an implementation described in U.S. Pat. No. 5,818,583, which is incorporated by reference herein, may be used.

Certain embodiments of the present invention may improve upon a frequency-domain photon migration (FDPM) the technique for measuring powder absorbance, which is described in Shinde, R. R.; Balgi, G. V.; Nail, S.; and E. M. Sevick-Muraca, "Frequency-domain photon migration measurements for quantitative assessment of powder absorbance: a novel sensor of blend homogeneity," J. Pharm. Sci., 88: 959–966, 1999, (hereinafter referred to as "Shinde") which is incorporated by reference herein. Shinde describes measurement of absorbance, but does not describe other characteristics of the powder bed that could be monitored by FDPM measurement that may be used to assess powder blending and downstream transport of powders.

Certain embodiments of the present invention provide a technique for monitoring tableting and particle blending processes, and for detecting changes in uniformity during the transfer or storage of powders. The technique separates absorption and scattering properties of the powder, providing direct measurement of active agent within a powder bed using the absorption property, a direct measurement of particle size and the uniformity of particles using the scattering property, and an indication of segregation effects from changes in the scattering property of the powder. The technique may be used to sample large volumes of powders, thus providing a low variance of measurement. Accordingly, the variation of blend uniformity with respect to particle size or active ingredient concentration can be statistically evaluated to determine uniformity of the powder bed. According to one embodiment, various wavelengths of incident light may be used to obtain spectral information for a number of constituents of a powder bed. Typically, the technique requires no external calibration.

One embodiment of the present invention may provide a non-invasive device for determining characteristics and uniformity of a powder. The device may be implemented in any of a number of suitable manners and may have any suitable features. For example, a device may be implemented as a hand-held probe or an in situ monitor within a blending instrument. As another example, a device may utilize wireless communication to enable remote sensing on, for example, a blending instrument. As yet further examples, a device may be disposable, may be battery operated, or may be available as a chip technology. Certain embodiments of the invention may include none, some, or all of the above technical advantages.

Figure 2:
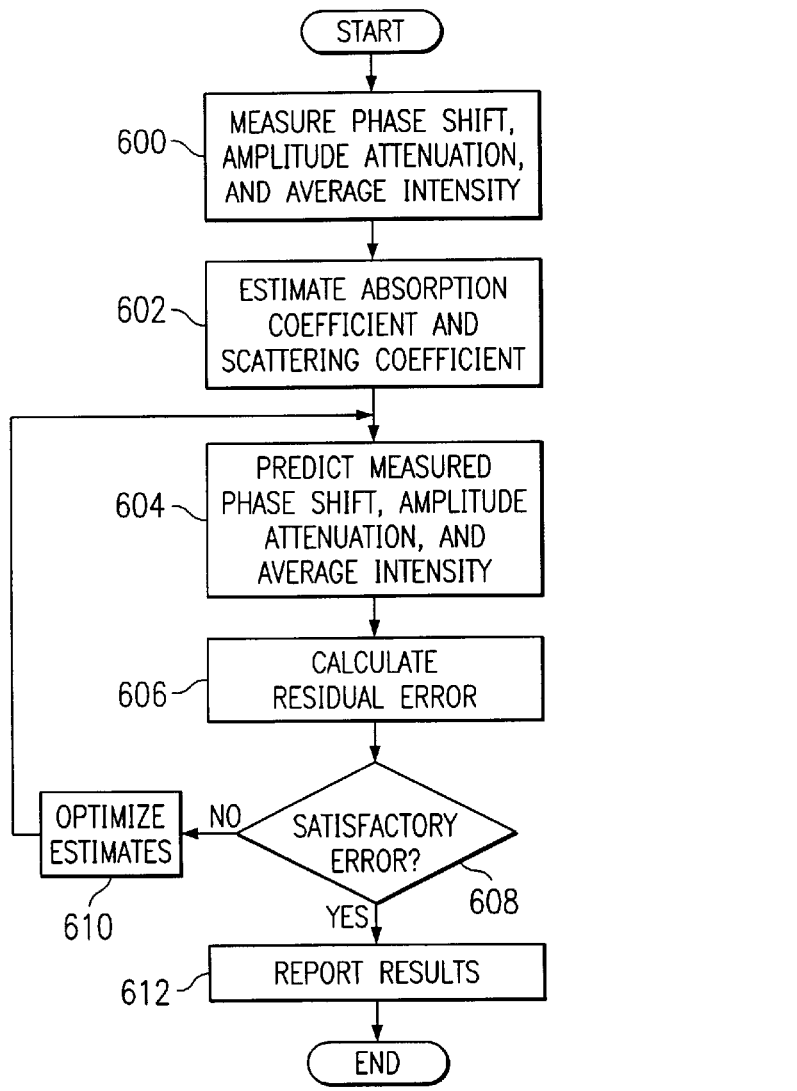
FIG. 2 is a flowchart illustrating one embodiment of a method for determining an absorption coefficient and an isotropic scattering coefficient.

FIG. 2 is a flowchart illustrating one embodiment of a method for determining absorption coefficient $\mu_a$ and isotropic scattering coefficient $\mu'_s$ from phase shift $\theta$ amplitude attenuation AC, and average intensity DC. In general, the method for determines absorption coefficient $\mu_a$ and isotropic scattering coefficient $\mu'_s$ by determining measured values for phase shift $\theta$, amplitude attenuation $I_{AC}$, and average intensity DC, estimating absorption coefficient $\mu_a$ and isotropic scattering coefficient $\mu'_s$, determining predicted values for phase shift $\theta$, amplitude attenuation AC, and average intensity DC from the estimated absorption coefficient $\mu_a$ and isotropic scattering coefficient $\mu'_s$, and comparing the predicted values with the measured values.

The method begins at step 600, where phase shift $\theta$, amplitude attenuation $I_{AC}$, and average intensity DC are measured as a function of source-detector separation, modulation frequency, or both to obtain measured values. Absorption coefficient $\mu_a$ and isotropic scattering coefficient $\mu'_s$ are estimated at step 602. Predicted values for phase shift $\theta$, amplitude attenuation AC, and average intensity DC are determined from the estimated absorption coefficient $\mu_a$ and isotropic scattering coefficient $\mu'_s$ at step 604. The predicted values may be determined according to solutions to diffusion equations or other mathematical relationship describing light propagation through powders. For example, for an infinite medium, the predicted values for phase shift $\theta$, amplitude attenuation $I_{AC}$, and average intensity DC of the modulated signals may be given by Equations (3) through (5):

$$\theta = \sqrt{\frac{\mu_a}{D}}\left(1 + \left(\frac{\omega}{\mu_a c}\right)^2\right)^{1/4} \sin\left(\frac{1}{2}\arctan\left(\frac{\omega}{\mu_a c}\right)\right) \cdot (2\rho) \quad (3)$$

$$\ln(2\rho \cdot DC) = \sqrt{\frac{\mu_a}{D}} \cdot (2\rho) + \ln\left(\frac{SA}{4\pi DC}\right) \quad (4)$$

$$\ln(2\rho \cdot AC) = \quad (5)$$
$$\sqrt{\frac{\mu_a}{D}}\left(1 + \left(\frac{\omega}{\mu_a c}\right)^2\right)^{1/4} \cos\left(\frac{1}{2}\arctan\left(\frac{\omega}{\mu_a c}\right)\right) \cdot (2\rho) + \ln\left(\frac{SA}{4\pi DC}\right)$$

where optical diffusion coefficient D is given by $$D = \frac{1}{3(\mu_a + \mu'_s)},$$

distance $2\rho$ [cm] is the separation between a source fiber and a detector fiber, c [cm·s$^{-1}$] is the speed of light, A [cm] is the modulation depth of the source, and S [photons·s$^{-1}$] is the fluence of a laser source.

The residual error Res is computed at step 606 according to Equation (6):

$$\text{Res} = \sum_{i,j} \left[\frac{(\theta_{ij} - \hat{\theta}_{ij}(\mu_a, \mu'_s))^2}{\sigma_\theta^2}\right] + \left[\frac{(DC_{ij} - D\hat{C}_{ij}(\mu_a, \mu'_s))^2}{\sigma_{DC}^2}\right] + \quad (6)$$
$$\left[\frac{(I_{ACij} - I_{ACij}(\mu_a, \mu'_s))^2}{\sigma_{AC}^2}\right]$$

where the summation is taken over different source-detector separations i and modulation frequencies j; $\sigma$ is the standard deviation of the measurement; and $\theta_{ij}$, $DC_{ij}$, and $I_{ACij}$ and $\hat{\theta}_{ij}$, $D\hat{C}_{ij}$ and $\hat{I}_{ACij}$ are the measured and predicted values of phase shift, average intensity, and amplitude attenuation, respectively.

If residual error Res is not satisfactory at step 608, the method proceeds to step 610 to optimize the estimates of absorption coefficient $\mu_a$ and isotropic scattering coefficient $\mu'_s$. The estimates may be optimized by minimizing residual error Res. After optimizing the estimates, the method returns to step 604 to determine predicted values for phase shift $\theta$, amplitude attenuation $I_{AC}$, and average intensity DC from the optimized estimates. If residual error Res is satisfactory at step 608, the method proceeds to step 612 to report the results. After reporting the results, the method terminates.

FIG. 3 is a block diagram illustrating one embodiment of a system 500 for determining characteristics of a powder bed P. In general, system 500 utilizes a laser diode and heterodyned fast detector system to achieve FDPM measurements enabling FDPM parameters to determine characteristics of powder bed P.

Specifically, system 500 includes a light source 530. According to one embodiment, light source 530 may comprise a laser source 531 and a laser source driver 532. Laser source 531 may comprise, for example, an array of laser diodes, laser emitting diode, or other source which can be modulated, and laser source driver 532 may comprise a diode array driver, laser emitting diode driver, or other source driver. Laser source driver 532 provides signal energy that is directly modulated by a radio frequency (RF) signal at frequency ω produced by a frequency synthesizer 534. The RF signal results in an intensity modulated beam 536 from laser source 531. An alternative embodiment of light source 530 is described with reference to FIG. 4.

Figure 4:
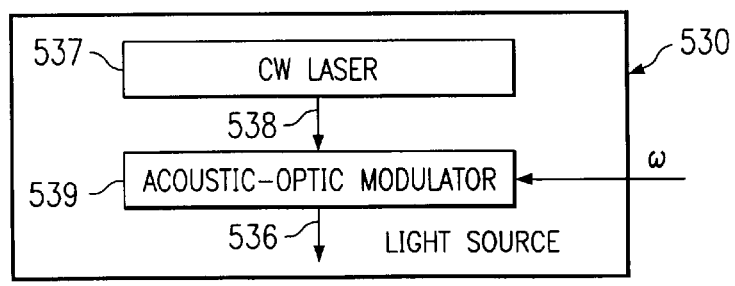
FIG. 4 is a block diagram illustrating an embodiment of a light source.

FIG. 4 is a block diagram illustrating another embodiment of light source 530. Light source 530 may comprise a continuous wave (CW) laser 537 that generates a beam 538. Beam 538 is focused into an acousto-optic modulator 539 that is driven by a radio frequency (RF) signal at frequency ω produced by a frequency synthesizer 534. The RF signal results in an intensity modulated beam 536 from acousto-optic modulator 539 at the same frequency.

Referring back to FIG. 3, beam 536 may be directed to beam splitter 544, which splits beam 536. Beam 536 may be split such that approximately 80 percent of beam 536 is directed along a source fiber 546 to a sample interface 550 and the remaining portion of beam 536 is directed along a fiber (or path) 548 to a reference detector 549. Sample interface 550 interfaces the delivery of light to a powder bed P. The particles of powder bed P multiply scatter the modulated light from source fiber 546. A detector fiber 552 collects the modulated scattered light and directs the modulated scattered light to a sample photodetector 554. Sample photodetector 554 may comprise, for example, a photomultiplier tube or any other fast sensor suitable for detecting modulated light. Fibers 546, 548, and 552 may comprise optical fibers or other fibers suitable for transmitting light.

Reference detector 549 and sample detector 554 serve as detectors and mixers. Under the direction of a processor 562, frequency synthesizer 563 generates a radio frequency (RF) signal at a frequency ω+Δω that is used to gain modulate reference detector 549 and sample detector 554. Frequency synthesizer 563 may be phase-locked to frequency synthesizer 534 via a 10 megahertz synchronization signal. Accordingly, reference detector 549 and sample detector 554, which collect optical signals modulated at frequency ω, produce low frequency signals at modulation frequency Δω, which is typically on the order of kilohertz. The output of reference detector 549 and sample detector 554 provides information about the phase, amplitude, and average intensity of the optical signals modulated at frequency ω.

Mixed signals from reference detector 549 and sample detector 554 are sent to processor 562 to provide information about phase shift θ, amplitude attenuation $I_{AC}$, and average intensity of the modulated signal DC at modulation frequency ω. By varying the wavelength of the light provided by source 530, the phase shift θ, amplitude attenuation $I_{AC}$, and average intensity of the modulated signal DC may be obtained as a function of the wavelength. According to one embodiment, the modulation frequency ω may be approximately 100 kilohertz to 300 megahertz, while the cross correlation frequency Δω may be approximately on the order of 10 hertz to 100 kilohertz.

Processor 562 receives signals from reference detector 549 and sample detector 554 via an analog-to-digital converter 570. Analog-to-digital converter 570 may comprise a data acquisition module suitable for digitizing output from reference detector 549 and sample detector 554. Processor 562 may send a control signal to frequency synthesizers 534 and 563 to change the values of ω and ω+Δω in tandem. In addition, processor 562 may provide output to change the position of detector fiber 552 relative to the position of source fiber 546, or accept signals from one of a number of sample detectors 554 replicated to measure FDPM parameters as a function of distance 2ρ, away from the incident point source of light.

Processor 562 may comprise any suitable device operable to accept input, process the input according to predefined rules, and produce output, for example, a personal computer, a series of circuits, or any other suitable processing device. Processor 562 may determine the characteristics of the powder bed according to the methods described with reference to FIGS. 12 and 13. Examples of output from system 500 are described with reference to FIGS. 5, 6, and 7.

System 500 may be practiced in any of a number of suitable manners. For example, modulated light may be delivered using of fiber optics, and scattered light may be collected using fiber optics or other detector directly positioned at an interface with the powder bed. Other techniques for delivery and collection, however, may be used. For example, point illumination may be used with area detection using an array of detectors or charge-coupled device over the surface of the powder bed. As another example, area illumination with an expanded laser diode beam or an array of diodes may be used.

As yet another example, a single oscillator may be used to drive laser source 531 and photodetector 554 at the same modulation frequency. The DC level of the detector signal varies as a function of the phase delay between the modulation of laser source 531 and photodetector 554 according to the optical properties of powder bed P. As a variable phase delay between the RF signals of frequency synthesizers 534 and 563 that is manipulated between 0 and 2π is introduced, the DC level of the detector signal maps out a sine wave from which amplitude attenuation and phase delay information can be obtained, and the optical properties of the powder bed P can be determined.

Certain embodiments of system 500 may include technical advantages. For example, the measurements of phase-shift θ', amplitude attenuation $I_{AC}$, and average of the modulated signal DC do not require external calibration with an external reference standard. In addition, absorption coefficient $\mu_a$ and isotropic scattering coefficient $\mu'_s$ are obtained as separate parameters rather than as a single product, allowing for calculation of uniformity characteristics of powder bed according to the methods described in FIGS. 12 and 13. Furthermore, system 500 may be used to measure a significant volume of powder that can be directly determined from the measurements, so that the natural variance of measurements may be lower than for measurements obtained using other optical measurement approaches such as near-infrared (NIR) spectroscopy and (LIF) laser induced fluorescence. Accordingly, the variance of the measurements may be used as a measure of blend uniformity for regulatory purposes.

Figure 5:
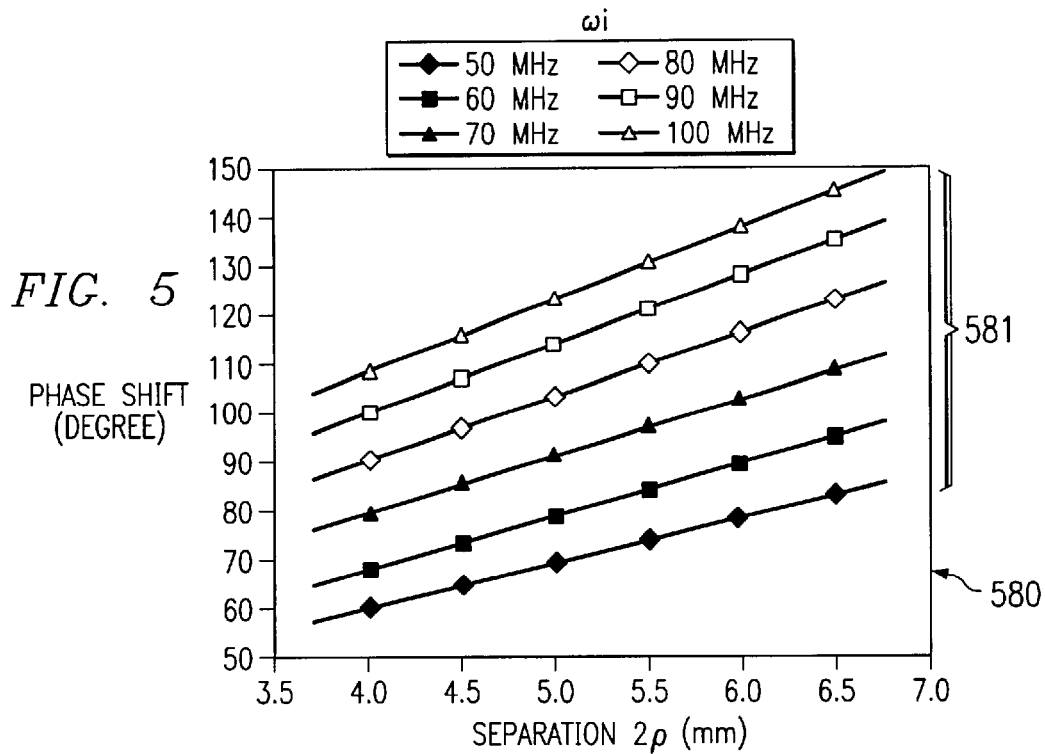
FIGS. 5, 6, and 7 illustrate example measurements of phase shift, amplitude attenuation, and average intensity.
Figure 6:
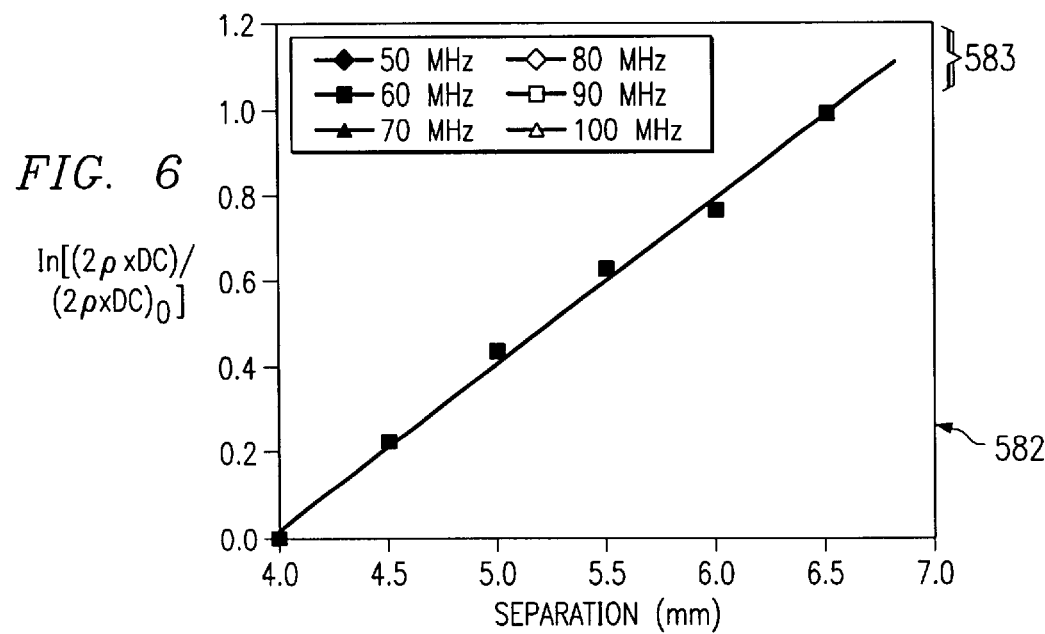
Figure 7:
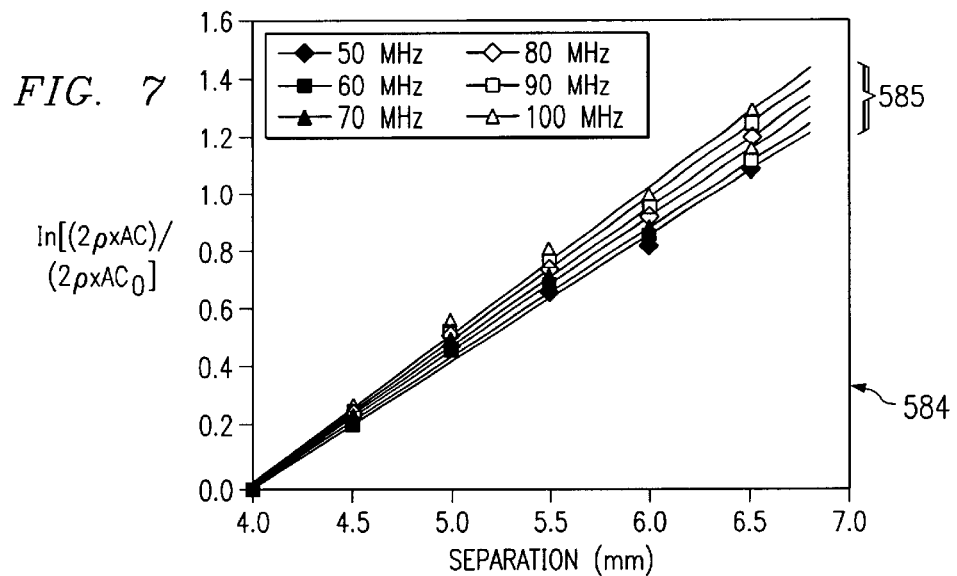

FIGS. 5, 6, and 7 illustrate example measurements of phase shift θ, amplitude attenuation $I_{AC}$, and average intensity of the modulated signal DC as a function of distance 2ρ between source and a detector and as a function of the modulation frequency of a powder bed. The sample powder comprised small particles with a mean diameter of 280 μm. FIG. 5 is a diagram 580 illustrating example measurements of phase shift θ, FIG. 6 is a diagram 582 illustrating example measurements of $\ln[(2\rho \cdot DC)/(2\rho \cdot DC)_0]$, and FIG. 7 is a diagram 584 illustrating example measurements of $\ln[(2\rho \cdot AC)/(2\rho \cdot AC)_0]$ as a function of the separation distance 2ρ. The subscript value denotes measurements made at a reference position, for example, a distance 2ρ equivalent to four millimeters.

Lines 581, 583, 585 denote the best fit from the solution of a photon diffusion equation, which may be described by Equations (3) through (5) described with reference to FIG. 2, from which the properties of absorption and scattering may be determined. The linearity of the data demonstrates the applicability of photon diffusion theory and the uniformity of each measured sample. Other mathematical models can be used to determine other characteristics of the powder bed such as the shape and volume fraction or the packing density of the powder.

Figure 8:
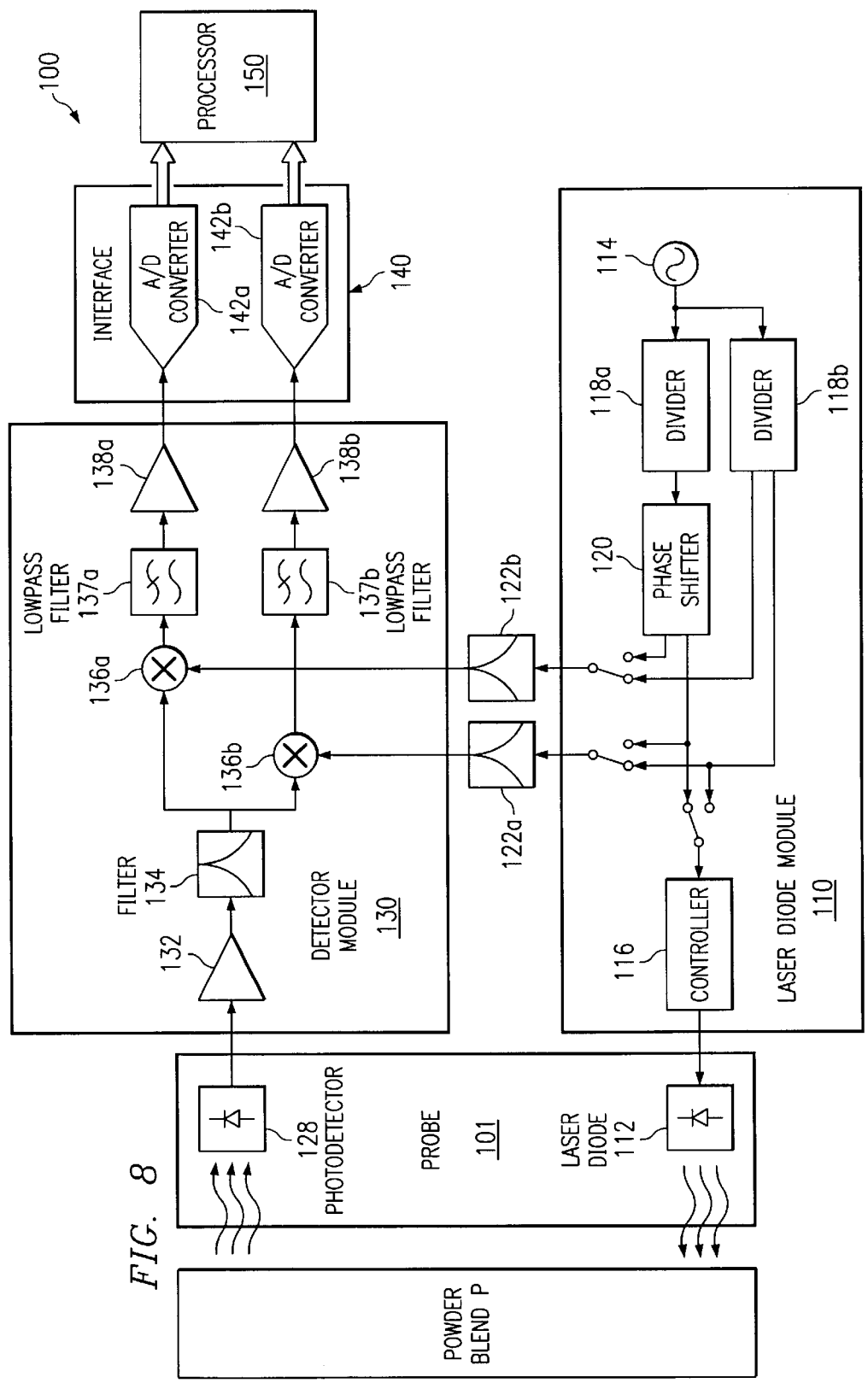
FIG. 8 is a block diagram illustrating one embodiment of yet another system for determining characteristics of a powder bed.

FIG. 8 is a block diagram illustrating one embodiment of yet another system 100 for characterizing a powder. In general, system 100 utilizes a modulated laser diode, a fast detector, and mixed signals to achieve frequency-domain photon migration, and measures frequency-domain photon migration parameters to determine characteristics of powder bed P. Techniques for mixing signals while preserving the time-varying content of the detected light include, for example, homodyne, heterodyne, I&Q, and single sideband techniques among others.

System 100 includes an interfacing probe 101 that may be used to readily characterize a powder by inserting probe 101 into the powder. Alternatively, probe 101 may be coupled to a blender holding the powder such that probe 101 comes in contact with the powder. In general, one or more laser source modules 110 control one or more laser sources 112 to generate light having a time varying intensity that interacts with a powder bed P. Laser source 112 may comprise a laser diode or a laser emitting diode, and laser source module 100 may comprise a laser diode module or a laser emitting diode module. One or more fast photodetectors 128 detect light that has interacted with powder bed P and generates a signal in response to the detected light. A detector module 130 and an interface 140 condition and convert the signals, and a processor 150 processes information from the signal to determine characteristics of powder bed P.

Specifically, system 100 includes one or more laser source modules 110 that each have an oscillator 114. Oscillator 114 generates an oscillating signal, and may comprise, for example, a 90 megahertz crystal oscillator. Dividers 118 divide the frequency of the signal by, for example, two, and may comprise, for example D flip-flops. A phase shifter 120 generates a phase shift of, for example, 90 degrees, from the signal, and may comprise, for example, a passive resistance-capacitance network implemented using resistors and capacitors with a tolerance of one percent. The signal is divided into a modulation signal sent to controller 116 and a reference signal sent to detector module 130.

Controller 116 uses the modulation signal to modulate laser source 112. Controller 116 may be implemented using Schmitt triggers. A Schmitt trigger may be used as an oscillator to generate a calibration time base. One-shot circuits use Schmitt triggers to generate two consecutive pulses in accordance with the calibration time base, which are used to calibrate bias and write pulse signals. Controller 116 supplies the modulation signal to laser source 112 in accordance with the write pulse signal. The modulation signal is not supplied while the bias and write calibration is taking place, so a circuit may be used to insert the proper levels to the modulation signal during the calibration. Laser source module 110 and laser source 112 operate as a source that provides photons that interact with a powder.

Probe 101 provides the optical interface between system 100 and powder bed P. Probe 101 may comprise one or more photodetectors 128 and one or more laser sources 112. Alternatively, probe 101 may comprise fiber optics that are connected to one or more photodetectors and one or more laser diodes external to probe 101. Laser source 112 generates photons that interact with powder bed P, and may comprise, for example, a 70 milliwatt laser diode. Photodetector 128 detects photons that have interacted with powder bed P, and generates a detector signal in response to detecting the photons. Photodetector 128 may comprise, for example, a silicon positive-intrinsic-negative (PIN) photodiode or an avalanche photodiode.

Detector module 130 conditions the detector signal received from photodetector 128 and the reference signal received from laser source module 110, and may include an amplifier 132 and a filter 134. Amplifier 132 amplifies the detector signal and may be used to couple the output impedance of photodetector 128 and the input impedance of filter 134. For example, amplifier 132 may be used to couple a photodetector 128 that requires an output impedance matched to 500Ω and a filter 134 that requires an input impedance matched to 50Ω. Filter 134 may comprise, for example, a surface acoustic wave (SAW) filter.

Detector module 130 receives the reference signal through filters 122. Filters 122 equalize the phase shift of the reference signal with the phase shift of the detector signal introduced by filter 134, and attenuate the reference signal to a level suitable for mixers 136. Filters 122 may also reduce the harmonic content of the reference signal. Filters 122 may comprise, for example, surface acoustic wave (SAW) filters. Mixers 136 combine the detector signal and the reference signal. Lowpass filters 137 may be used to reduce a 90 megahertz tone resulting from the mixing operation. Amplifiers 138 amplify the signal. Detector module 130 operates as a detector that detects photons that have interacted with a powder.

An interface 140 comprising analog-to-digital converters 142 converts analog signals from detector module 130 to digital signals. A processor 150 processes information from the signals to determine characteristics of powder bed P. Processor 150 may determine the characteristics according to the methods described with reference to FIGS. 12 and 13.

Figure 9:
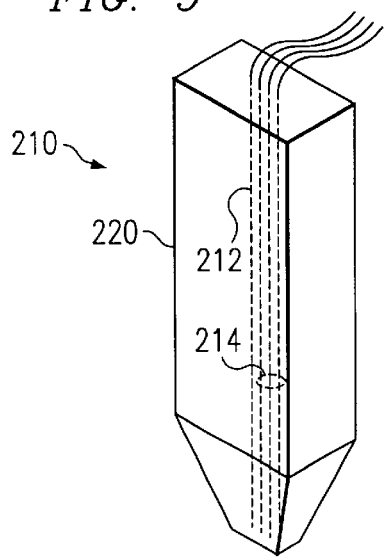
FIG. 9 illustrates one embodiment of a probe.

FIG. 9 illustrates one embodiment of a probe 101. Probe 101 can include one or more source fibers 212 and one or more detector fibers 214 coupled to a frame 220. Alternatively, probe 101 can include one or more laser sources 112 or one or more photodetectors 214 coupled to frame 220. Probe 101 may be hand held or otherwise used as a portable device.

Probe 101 may be implemented in any of a number of suitable ways. According to one embodiment, a light source wavelength identification may be encoded in the modulation frequency to enable simultaneous multiple wavelength FDPM measurements. For example, probe 101 may be supplied by different wavelength laser diodes driven by oscillator signals at slightly different modulation frequencies, resulting in multiple wavelength frequency-domain photon migration measurements at a single detector fiber 214. The measurements may be analyzed using fast Fourier transforms to recover the phase delay and amplitude attenuation of the modulation at each light source wavelength.

According to another embodiment, the position of source fiber 212 relative to a detector fiber 214 may be encoded within the modulation frequency of a laser diode associated with source fiber 212. For example, probe 101 may include multiple source fibers 212 located different distances from a single detector fiber 214. The laser diodes coupled to source fibers 212 may be modulated at slightly different frequencies. The signals from the laser diodes may be detected simultaneously and identified through fast Fourier transform analysis to determine the phase delay and amplitude information at each modulation frequency.

Other radio frequency mixing strategies may be used to monitor the characteristics of powder bed P. Specific incident light source wavelengths may be employed for optimally detecting absorption or even fluorescent emission of the constituents of powder bed P. For example, if a laser diode comprises a 1300 nanometer or 1550 nanometer laser diode, absorbance due to water in powder bed P may be assessed in pharmaceutical drying operations. In addition, the measurements may be multiplexed using light sources of various wavelengths to obtain spectral information to determine the constituents of powder bed P.

Probe 101 may have more, fewer, or other features. For example, all or portions of probe 101 may be implemented with complementary metal-oxide semiconductor (CMOS) technology. Probe 101 may communicate with a processor using wireless communication technology such as Bluetooth. Disposable probes 101 or probes 101 with disposable protective sleeves may be developed, making cleaning of probes 101 during pharmaceutical validation obsolete.

Figure 10:
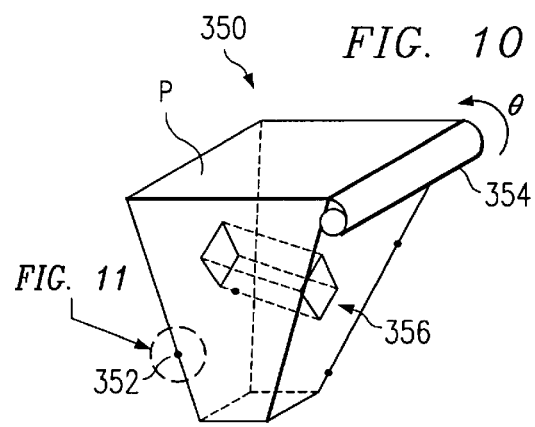
FIG. 10 is a diagram illustrating a rotating blender having a probe.

FIG. 10 is a diagram illustrating a rotating powder blender 350 with one or more probes 352 to provide in situ FDPM measurement during processing. Probe 352 may be used to emit and detect photons in order to determine characteristics of a powder bed P. Probe 352 is described in more detail with reference to FIG. 11. Rotating blender 350 includes a rotating shaft 354 and an internal prism cut-outs which are commonly used in tote blenders to enhance mixing of powder bed P. A number n of locations may be measured within the powder bed by coupling n probes to the blender. Alternatively, for impromptu validation, the probe may be stabbed by hand at a number n of different locations for measurements at n locations within the powder bed.

Figure 11:
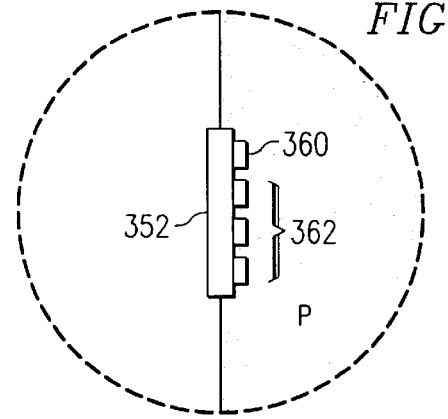
FIG. 11 is a diagram illustrating one embodiment of probe of the rotating blender of FIG. 10.

FIG. 11 is a diagram illustrating one embodiment of probe 352 interfacing with the powder bed P of the rotating blender 350 of FIG. 10. Probe 352 includes one or more sources 360 for emitting photons and one or more detectors 362 for detecting photons. Probe 352 may be coupled to the body of blender 350 with an optical window or other appropriate interface for accessing the powder bed P. Measurements may be conducted with the on-board sensor and can be transmitted through wireless communication to a central processor.

Figure 12:
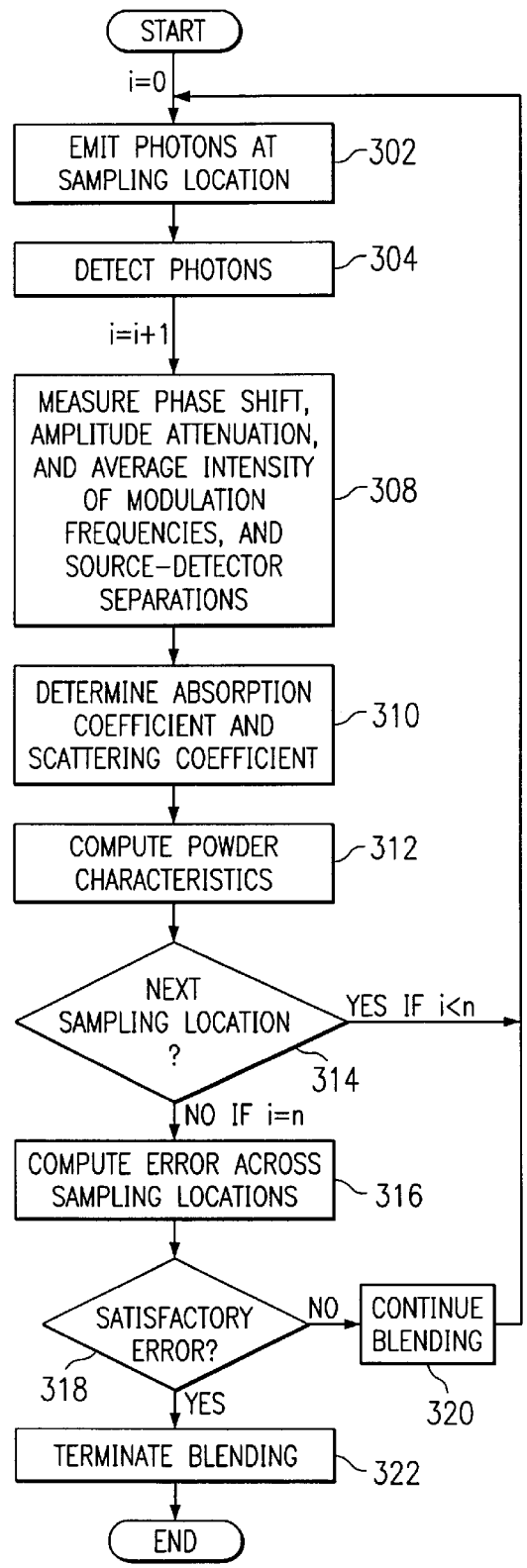
FIG. 12 is a flowchart illustrating one embodiment of a method for determining characteristics of a powder bed.

FIG. 12 is a flowchart illustrating one embodiment of a method for analyzing and determining the uniformity of a powder bed P. Uniformity with respect to the dispersion of an ingredient such as an active ingredient within powder bed P or uniformity with respect to the sizes of the particles of powder bed P may be determined.

The method begins at step 302, where photons are emitted at a sampling location i of n sampling locations of powder bed P that is being blended. As the light propagates through powder bed P, the amplitude of the light is attenuated by an amplitude attenuation $I_{AC}$ relative to the incident light, and the phase of the light is phase delayed by a phase shift θ. The photons are detected at step 304.

Steps 302 and 304 may be performed using a probe having a source fiber that emits photons and a detector fiber that detects photons. For each iteration of steps 302 and 304, the probe may be placed at different locations of powder bed P. Alternatively, steps 302 and 304 may be performed by one or more probes mounted to a rotating blender. An iteration of steps 302 and 304 may correspond to one or more rotations. The probes are stationary with respect to the blender, but powder bed P moves during the blending process, so the probes are placed at different sampling locations of powder P at each rotation.

The phase shift θ, amplitude attenuation $I_{AC}$, and average intensity of the modulated signal DC are measured at each location i at step 308. The measurements may be made as a function of the separation $\rho_k$ between the source fiber and detector fiber, the modulation frequency ω, or both. Optical properties such as absorption coefficient $\mu_a$ and isotropic scattering coefficient $\mu'_s$ are determined from phase shift θ, amplitude attenuation $I_{AC}$, and average intensity DC at step 310. Absorption coefficient $\mu_a$ indicates the ability of a substance to absorb light of a particular wavelength, and the isotropic scattering coefficient $\mu'_s$ indicates the ability of a substance to scatter light of a particular wavelength. An example of a method for determining absorption coefficient $\mu_a$ and isotropic scattering coefficient $\mu'_s$ from phase shift θ, amplitude attenuation $I_{AC}$, and average intensity DC is described with reference to FIG. 2.

Powder characteristics are computed at step 312. Powder characteristics may include the uniformity of an ingredient, the uniformity of particle size, the volume of powder sampled, as well as other attributes such as the powder packing density or shape characteristics. A method for computing powder characteristics is described with reference to FIG. 13.

If there is a next sampling location at step 314, the method returns to step 302 to emit photons at the next sampling location. If there is no next sampling location at step 314, the method proceeds to step 316.

Variation of the measurements of absorption and scattering properties or of powder characteristics made at different locations of a powder bed or at different times provides an indication of the blend uniformity. The error for the variation of measurements is computed at step 316. The error may provide an indication of the uniformity of a powder characteristic. If the error is not satisfactory at step 318, the method proceeds to step 320 to continue blending powder bed P and then to step 302 to emit photons at a next sampling location. If the error is satisfactory at step 320, the method proceeds to step 322 where blending is terminated. After blending is terminated, the method terminates.

Figure 13:
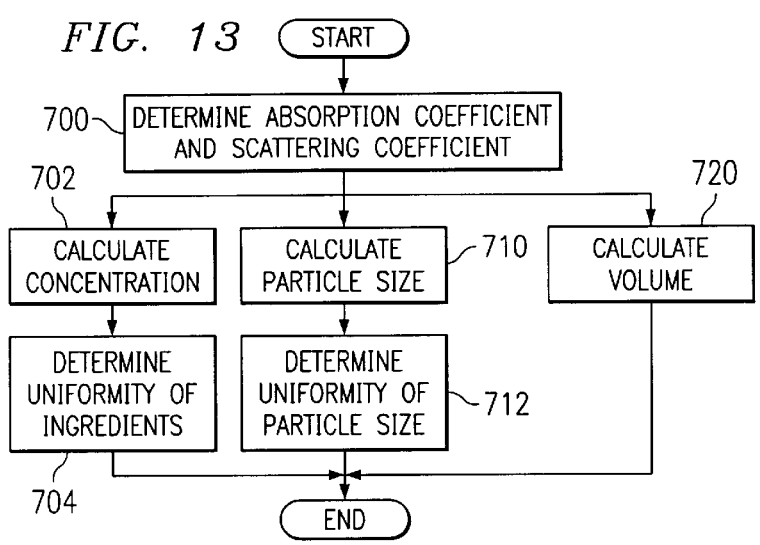
FIG. 13 is a flowchart illustrating one embodiment of a method for computing powder characteristics.

FIG. 13 is a flowchart illustrating one embodiment of a method for computing powder characteristics. The method may be used to calculate characteristics such as the uniformity of an ingredient, the uniformity of particle size, the volume of powder sampled, or any combination of the preceding. The method begins at step 700, where absorption coefficient $\mu_a$ and isotropic scattering coefficient $\mu'_s$ are determined from the diffusion approximation or another approximation to the radiative transport equation.

If the uniformity of an ingredient is to be determined, the method proceeds to step 702 to calculate the concentration [C] of an ingredient according to absorption coefficient $\mu_a(\lambda)$. Absorption coefficient $\mu_a(\lambda)$ at wavelength λ is given by Equation (7):

$$\mu_a(\lambda) = \epsilon(\lambda) \cdot [C] + \mu_a^0(\lambda) \tag{7}$$

where $\mu_a^0(\lambda)$ is the absorption of the excipient powder, and $\epsilon(\lambda)$ is an extinction coefficient.

If the components of the excipient powder are well mixed or consist of one component, then $\mu_a^0(\lambda)$ is constant. The wavelength of light that is absorbed maximally by the ingredient has the highest extinction coefficient and yields measurements that are highly sensitive to changes in the ingredient.

If the concentration of k ingredients is to be determined, then the extinction coefficients $\epsilon_k^j$ for each ingredient k at each wavelength j for a number of wavelengths are determined. The concentration $[C_k]$ of ingredient k may be calculated according to Equation (8):

$$\mu_a(\lambda_j) = \sum_i \epsilon^j k(\lambda_j) \cdot [C_k] \tag{8}$$

Example measurements of concentration are described with reference to FIG. 14. The dimensionless absorbance is given by the differential absorption of a low weight % of a low dose active ingredient relative to the absorption of the excipient ingredient.

The uniformity of one or more ingredients of powder bed P is determined from the one or more ingredient concentrations [C] at step 704. Homogeneity may be assessed in terms of the spatial deviation $\sigma_{blend}^2$ end of each ingredient concentration $[C_k]$ across n sampling locations i of powder bed P, as expressed by Equation (9):

$$\sigma_{k_{blend}}^2 = \frac{\sum_i ([C_{k_i}] - [\overline{C_k}])^2}{n-1} \tag{9}$$

Spatial deviation $\sigma_{kblend}^2$ for component k is the sum of sampling variance $\sigma_{sample}^2$ and instrumental error $\sigma_{precision}^2$. For frequency-domain photon migration, spatial deviation $\sigma_{blend}^2$ is approximately equal to sampling variance $\sigma_{sample}^2$ due to the small instrumental error $\sigma_{precision}^2$ for frequency-domain photon migration measurements. Consequently, for a well-blended powder mixture, a limited number of samples may be used to predict $\sigma_{blend}^2$ with satisfactory precision. After determining the uniformity, the method terminates. Example concentration measurements from an actual low dose pharmaceutical mixing experiment are described with reference to FIGS. 15 and 16. Measurements of samples taken at different positions A, B, C, D, E within the powder bed are conducted as a function of blending time in a tote blender. The average and standard deviation of the FDPM measurements in comparison to HPLC measurement are compared in FIG. 16.

The final content of a pharmaceutical tablet may be affected by particle segregation due to non-uniformity. Accordingly, the assessment of particle size uniformity, which may indicate downstream segregation, may be important. If the uniformity of particle size is to be determined, the method proceeds to step 710 to calculate particle size from isotropic scattering coefficient $\mu'_s$. If the diameter d of the particles of powder bed P is greater than the wavelength of the incident light, then diameter d is independent of wavelength and may be approximated from isotropic scattering coefficient $\mu'_s$ according to Equation (10):

$$d = \alpha \frac{1}{\mu'_s} \quad (10)$$

where α is a constant factor determined independently. Examples of particle size measurements are described with reference to FIG. 17, which describes lactose powder beds of differing powder particle sizes measured according to the FDPM technique at different wavelengths. At wavelengths greater than the dimensions of the particle, the wavelength independence the relationship described by Equation (10) is evident. Consequently, from FDPM measurements of the isotropic scattering coefficient, the local mean size of particles may be computed from Equation (10).

The sizes of the particles at different locations within powder bed P are compared to determine the particle size uniformity of powder bed P at step 712. A large deviation among particle sizes at different locations indicates low uniformity, and a small deviation among particle sizes at different locations indicates high uniformity. The variance of mean particles sizes may be determined according to Equation (11):

$$\sigma^2_{blend} = \frac{\sum_i ([d_i] - [\overline{d}])^2}{n-1} \quad (11)$$

The variance may be compared to a critical value to assess the particle size uniformity of the powder bed P. After determining the uniformity, the method terminates.

Regulatory guidelines for the validation of blending processes typically require sample sizes on the order of one to three times the single dosage form, typically 100 to 1000 mg of powder mass or 0.5 to 5 cm³ of uncompressed powder. Accordingly, the volume of the powder sampled may need to be determined for regulatory purposes. If volume is to be determined, the method proceeds to step 720 to calculate the volume. At the time of measurement, the volume of powder interrogated as the intensity modulated light travels from one point to another at a powder interface may computed using Equation (12):

$$V(P) = \frac{2}{3}\pi\rho^3(\cosh^3\xi_{(P)} - \cosh\xi_{(P)}) \quad (12)$$

where the dimensional prolate spherical volume V(P) is defined by an outer most radius $\xi_{(P)}$. The outer most radius $\xi_{(P)}$ defined a region visited by photons that contribute to the signal generated by photon propagation from a source to a detector located distance 2ρ away. The outer most radius $\xi_{(P)}$ is implicitly a function of the noise level and the sensitivity of the detector for collecting photons from a volume sampled with cumulative probability P.

The cumulative probability P associated with photons contributing above the noise floor of typical detectors is generally between 0.9 and 0.97. The cumulative probability P may be experimentally determined and may be assumed constant for a specific device. The relationship defining the cumulative probability at a prolate spherical radius ξ within the powder bed is given by Equations (13):

$$P(\xi) = \frac{F(\xi)}{F(\infty)} \quad (13)$$

$$F(\xi) = \sum_{i=1}^{5} b_i E(\xi, h, i-3) +$$

$$\sum_{i=1}^{5}\sum_{j=1}^{4} e_i p_j (E(\xi Eh, i+j-4) +$$

$$d_1 E(\xi(h + d_2 i + j - 4))$$

where E is an exponential integral $$E(\xi, 2h, k) = \int_1^{\cosh\xi} e^{-2hv} v^k dv,$$

ν is an integration parameter, and h is given by $$h = \sqrt{\frac{m}{Dc}}\, \rho \cos\frac{\theta}{2},$$

where m is given by $m = \sqrt{(\mu_a c)^2 + \omega^2}$. Consequently, the outer most radius ξ corresponding to the maximum cumulative probability detected by the sensor may be computed and used in the formula provided by Equation (12) to provide a value of the sampled volume. After computing the volume, the method terminates. Clearly, as the modulation frequency, source-detector separation, and optical properties of the powder changes, the volume of powder sampled by FDPM techniques varies in a manner predicted by Equation (12).

From the volume sampled by the FDPM measurements and the desired target weight percent $C_k$ of a uniform blend, the minimum relative deviation of measurements (RTD) possible can be computed from the random component mixture model described by Equation (3) above using the following equation:

$$RTD_k = \sqrt{\sigma^2}/C_k$$

From the computed variance of the FDPM measurements described by Equation (9), the relative standard deviation can be computed for component k according to the following equation:

$$RTD_{k_{FDPM}} = \sqrt{\sigma_{kblend}^2}/C_k$$

The RTD may be computed using the value of the volume sampled by the FDPM measurements. If the measurement RTD approaches the theoretical minimum for a perfectly uniform mixture, then the powder bed can be considered to be uniform. Currently, FDA regulations state that blend content uniformity is achieved when the RTD is within 5% of the desired dose.

The methods described with reference to FIGS. 12 and 13 may be modified without departing from the scope of the invention. For example, some of the steps may be omitted or performed in a different order, and other steps may be added. In addition, the formulations provided here are generally derived, so the expressions may be applicable to continuous wave or intensity-based measurements (ω=0), as well as to any homogeneous medium that multiply scatters light.

Figure 14:
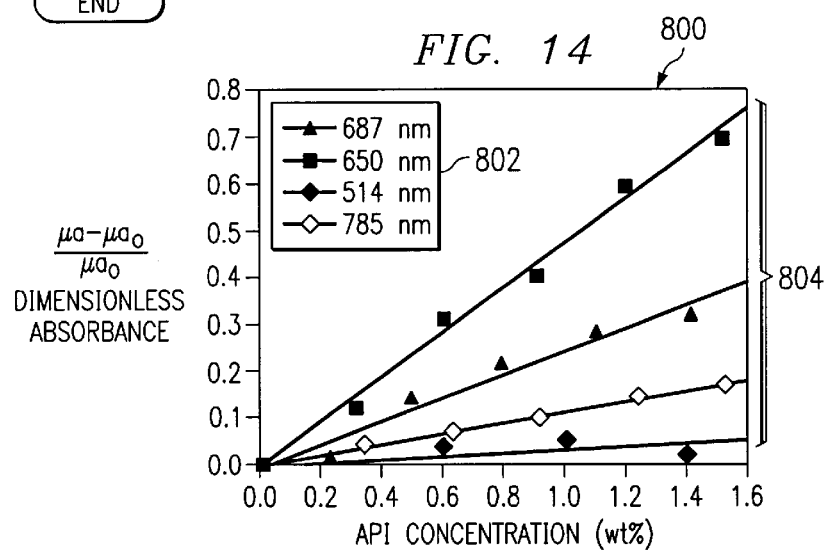
FIG. 14 is a diagram describing example measurements of dimensionless absorbance versus active pharmaceutical ingredient concentration.

FIG. 14 is a diagram 800 describing example measurements of dimensionless absorbance $[\mu_a(\lambda)-\mu_a^0(\lambda)]/\mu_a^0(\lambda)$ versus active pharmaceutical ingredient (API) concentration by percent weight of a Terazosin powder mixture at wavelengths of 514 nm (♦), 650 nm (■), 687 nm (▲), and 785 nm (◇). The components of the excipient powder are assumed to be well mixed and may be represented by a constant absorbance. Symbols 802 ♦, ■, ▲, and ◇ denote experimental measurements, and lines 804 denote the linear fit. The slope of each line 804 provides an extinction coefficient associated with the wavelength of the line 804. The wavelength of light that is absorbed maximally by the active pharmaceutical ingredient possesses the highest extinction coefficient and gives rise to the highest sensitivity to changes in the active pharmaceutical ingredients.

Figure 15:
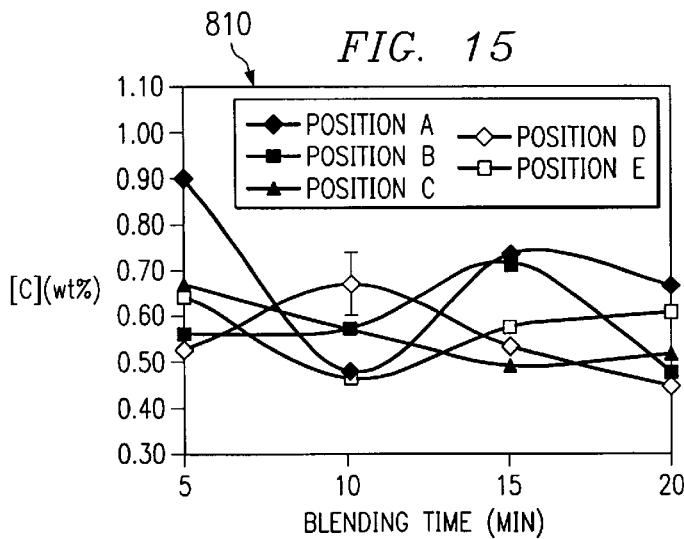
FIG. 15 is a diagram illustrating example measurements of concentrations of active ingredients versus blending time.

FIG. 15 is a diagram 810 illustrating example FDPM measurements of the concentrations of active ingredients versus blending time. According to the illustrated example, the concentration of a low dose pharmaceutical agent, Terazosin, was determined at 685 nanometers. The samples were taken from specific sampling locations within a rotating Gallay blender. The desired dosage of the formulation was 0.7wt %.

FIG. 16 is a diagram 820 illustrating examples of FDPM and HPLC measurements of active pharmaceutical ingredient concentrations versus blending time. The concentrations were determined according to the method described with reference to FIG. 13 as well as according to a high performance liquid chromatography (HPLC) technique. On the one hand, the high performance liquid chromatography measurements sample a significantly larger volume. On the other hand, the method of FIG. 13 samples smaller volumes that may be consistent with regulatory guidelines.

FIG. 17 is a diagram 830 illustrating example FDPM measurements of the scattering coefficient of a powder bed as a function of particle size. Diagram 830 provides an example of the relationship between measurements of isotropic scattering performed by the method of FIG. 13 and the reciprocal of the mean powder particle size at 828, 785, and 650 nanometers. At 650 nanometers, the wavelength of light becomes comparable to the particle sizes interrogated and exhibits a different constant factor α.

FIG. 18 is a diagram 840 illustrating example relative standard deviations of concentration versus sampled volumes as predicted by the complete random mixture model for a high dose ([A]=50 wt %) and a low dose ([A]=0.7 wt %). The relative standard deviation of concentration describes the standard deviation normalized against a nominal target dose concentration. The sampled volume may be used to determine if measurement variances are sufficiently small to assess content uniformity. The complete-random-mixture (CRM) model used to describe powder blends shows that the variance associated with measurement of discretely sampled powders is inversely proportional to the sampled volume in the case of a completely mixed sample. Consequently, the amount of sampled volume dictates the smallest measurement variance for a statistical evaluation of blend uniformity.

Near infrared (NIR) spectroscopy may be used to sample volumes of approximately 10 mg (~12 mm³) using a 4 mm diameter probe. On-line Fourier transform near infrared (FT-NIR) measurements using similar probe geometry may track mean contents with uncertainties of 20 to 30% of the mean active pharmaceutical ingredient content. Emerging laser-induced fluorescence (LIF) techniques may be expected to sample smaller volumes, and consequently may have even larger measurement variances.

Referring to FIG. 18, the complete-random-mixture model, represented by lines 842, indicates that the variance of component concentration measurements due to the limited number of discrete powders is inversely proportional to the sampled volume and the active pharmaceutical ingredient content. An example criteria for blend uniformity may be that the relative standard deviation of the measurement should be between the percentage predicted by the complete random mixture model and a regulatory guideline of, for example, 5%.

Example sampled volumes using a near infrared technique, the method of FIG. 13, and a high performance liquid chromatography (HPLC) technique are less than 0.2 cm³, around 1.5 cm³ at the modulation frequency of 50 MHz, and more than 300 cm³, respectively. Correspondingly, the relative deviations of the three types of measurements for a powder sample of 0.7 wt % active pharmaceutical ingredient content having an average particle diameter of 280 μm are estimated to be more than 8%, around 3%, and less than 1%, respectively.

Accordingly, the one component model predicts that the standard deviation of measurements cannot be lower than what is predicted by the sampled volume. The determination of the sampled volume by the method of FIG. 13 may be useful for determining optimal measurement variance associated with a perfectly mixed powder system. Consequently, the assessment of uniformity based upon absorption, scattering, content, or particle size may be provided with the computation of the sampled volume and the variance expected for a uniform system.

Certain embodiments of the invention may provide one or more technical advantages. A technical advantage of one embodiment may be that an absorption coefficient and an isotropic scattering coefficient for a powder are obtained as separate parameters rather than a single product. The separate parameters allow for estimation of characteristics describing of the powder. Another technical advantage of one embodiment may be that a probe that may be used to determine characteristics of a powder. The probe may be readily inserted into the powder or affixed to a rotating blender to provide convenient characterization of the powder.

Although an embodiment of the invention and its advantages are described in detail, a person skilled in the art could make various alterations, additions, and omissions without departing from the spirit and scope of the present invention as defined by the appended claims.

What is claimed is:

1. A method for characterizing a powder bed, comprising:
generating a plurality of measurements of a powder bed comprising a plurality of particles by repeating the following for each location of a plurality of locations of the powder bed:
illuminating a location of the powder bed with a light, the light having a time varying intensity with a resolution of less than one hundred nanoseconds, the particles scattering the light to alter the time varying intensity of the light;
detecting the light received from the powder bed, the light having propagated through a portion of the particles, the portion of the particles defining a sampled volume interrogated by the propagating light;
measuring the altered time-varying intensity of the light to generate a time-dependent signal, the time-dependent signal having a time-dependence less than or equal to a time-of-flight of a photon of the propagating light;

determining a measurement of an optical property of the powder bed according to the time-dependent signal using a mathematical model describing light propagation; and determining a measurement of a characteristic of the powder bed in accordance with the optical property;

determining the sampled volume interrogated by the propagating light;

calculating a variance associated with at least a subset of the measurements; and determining a uniformity associated with the powder bed in accordance with the variance and the sampled volume.

2. The method of claim 1, wherein:

determining a measurement of an optical property of the powder bed comprises calculating an absorption coefficient according to a light propagation equation; and determining a measurement of a characteristic of the powder bed in accordance with the optical property comprises determining a concentration of an ingredient of the powder bed in accordance with the absorption coefficient.

3. The method of claim 1, wherein:

determining a measurement of an optical property of the powder bed comprises calculating an isotropic scattering coefficient according to a light propagation equation; and determining a measurement of a characteristic of the powder bed in accordance with the optical property comprises determining a particle size of a particle of the powder bed in accordance with the isotropic scattering coefficient.

4. The method of claim 1, wherein:

determining a measurement of an optical property of the powder bed comprises:

calculating an isotropic scattering coefficient according to a light propagation equation; and calculating an absorption coefficient according to the light propagation equation; and determining a measurement of a characteristic of the powder bed in accordance with the optical property comprises:

determining a particle size of a particle of the powder bed in accordance with the isotropic scattering coefficient; and determining a concentration of an ingredient of the powder bed in accordance with the absorption coefficient.

5. The method of claim 1, wherein determining a measurement of a characteristic of the powder bed in accordance with the optical property comprises calculating an absorption coefficient in accordance with the selected member.

6. The method of claim 1, wherein:

illuminating a location of the powder bed with a light comprises illuminating the location of the powder bed with a periodic, time-varying modulated light;

measuring the altered time-varying intensity of the light to generate a time-dependent signal comprises determining a member selected from a group consisting of a phase shift, an average of the time varying intensity, and an amplitude associated with the altered time-varying intensity; and determining a measurement of a characteristic of the powder bed in accordance with the optical property comprises calculating an absorption coefficient in accordance with the selected member.

7. The method of claim 1, wherein determining a measurement of a characteristic of the powder bed in accordance with the optical property comprises calculating an isotropic scattering coefficient in accordance with the selected member.

8. The method of claim 1, wherein:

illuminating a location of the powder bed with a light comprises illuminating the location of the powder bed with a periodic, time-varying modulated light;

measuring the altered time-varying intensity of the light to generate a time-dependent signal comprises determining a member selected from a group consisting of a phase shift, an average of the time varying intensity, and an amplitude associated with the altered time-varying intensity; and determining a measurement of a characteristic of the powder bed in accordance with the optical property comprises calculating an isotropic scattering coefficient in accordance with the selected member.

9. The method of claim 1, wherein determining a uniformity associated with the powder bed in accordance with the variance and the sampled volume comprises:

determining a variance threshold for a perfectly mixed powder bed according to the sampled volume and a target concentration;

evaluating whether the variance satisfies the variance threshold for the perfectly mixed powder bed; and determining the uniformity associated with the powder bed in accordance with the evaluation.

10. The method of claim 1, wherein:

illuminating a location of the powder bed with a light comprises using a plurality of wavelength sources, each wavelength source modulated with an identifiable intensity modulation;

detecting the light received from the powder bed comprises detecting the light having a plurality of modulation frequencies at a detector;

measuring the altered time-varying intensity of the light to generate a time-dependent signal comprises separating the modulation frequencies and generating a time dependant signal for each modulation frequency and each wavelength; and determining a measurement of a characteristic of the powder bed in accordance with the optical property comprises determining a characteristic.

11. The method of claim 1, wherein:

illuminating a location of the powder bed with a light comprises illumination the location with a light having a plurality of modulation frequencies; and detecting the light received from the powder bed comprises detecting the light having the plurality of modulation frequencies, the light at each modulation frequency describing a measurement of the characteristic.

12. The method of claim 1, wherein:

illuminating a location of the powder bed with a light comprises using a plurality of sources, each source operable to generate light at a different modulation frequency, the sources generating light having a plurality of modulation frequencies; and detecting the light received from the powder bed comprises detecting the light having the plurality of modulation frequencies using a detector, each source associated with a different source-detector distance, the light at each frequency describing a measurement of the characteristic associated with a source-detector distance.

13. The method of claim 1, wherein:
illuminating a location of the powder bed with a light comprises interfacing a probe with the powder bed, the probe comprising a source operable to generate the light; and
detecting the light received from the powder bed comprises detecting the light using the probe comprising a detector operable to detect the light.

14. The method of claim 10, wherein the probe comprises a disposable probe.

15. The method of claim 1, wherein:
illuminating a location of the powder bed with a light comprises directing the light towards a location of the powder bed using a source operable to generate the light, the source moving with respect to the location of the powder bed, the source coupled to a receptacle, the powder bed disposed within the receptacle; and
detecting the light received from the powder bed comprises detecting the light using a detector operable to generate the light, the detector coupled to the receptacle.

16. The method of claim 1, wherein the characteristic of the powder bed comprises an element selected from a group consisting of particle packing density and particle shape.

17. A system for characterizing a powder bed, comprising:
a source operable to illuminate a location of the powder bed with a light, the light having a time varying intensity with a resolution of less than one hundred nanoseconds, the particles scattering the light to alter the time varying intensity of the light;
a detector operable to detect the light received from the powder bed, the light having propagated through a portion of the particles, the portion of the particles defining a sampled volume interrogated by the propagating light; and
a processor coupled to the source and the detector and operable to:
generate a plurality of measurements of a powder bed comprising a plurality of particles by repeating the following for each location of a plurality of locations of the powder bed:
measure the altered time-varying intensity of the light to generate a time-dependent signal, the time-dependent signal having a time-dependence less than or equal to a time-of-flight of a photon of the propagating light;
determine a measurement of an optical property of the powder bed according to the time-dependent signal using a mathematical model describing light propagation; and
determine a measurement of a characteristic of the powder bed in accordance with the optical property;
determine the sampled volume interrogated by the propagating light;
calculate a variance associated with at least a subset of the measurements; and
determine a uniformity associated with the powder bed in accordance with the variance and the sampled volume.

18. The system of claim 17, wherein the processor is operable to:
determine a measurement of an optical property of the powder bed by calculating an absorption coefficient according to a light propagation equation; and
determine a measurement of a characteristic of the powder bed in accordance with the optical property by determining a concentration of an ingredient of the powder bed in accordance with the absorption coefficient.

19. The system of claim 17, wherein the processor is operable to:
determine a measurement of an optical property of the powder bed by calculating an isotropic scattering coefficient according to a light propagation equation; and
determine a measurement of a characteristic of the powder bed in accordance with the optical property by determining a particle size of a particle of the powder bed in accordance with the isotropic scattering coefficient.

20. The system of claim 17, wherein the processor is operable to:
determine a measurement of an optical property of the powder bed by:
calculating an isotropic scattering coefficient according to a light propagation equation; and
calculating an absorption coefficient according to the light propagation equation; and
determine a measurement of a characteristic of the powder bed in accordance with the optical property by:
determining a particle size of a particle of the powder bed in accordance with the isotropic scattering coefficient; and
determining a concentration of an ingredient of the powder bed in accordance with the absorption coefficient.

21. The system of claim 17, wherein the processor is operable to determine a measurement of a characteristic of the powder bed in accordance with the optical property by calculating an absorption coefficient in accordance with the selected member.

22. The system of claim 17, wherein:
the source is operable to illuminate a location of the powder bed with a light by illuminating the location of the powder bed with a periodic, time-varying modulated light; and
the processor is operable to:
measure the altered time-varying intensity of the light to generate a time-dependent signal by determining a member selected from a group consisting of a phase shift, an average of the time varying intensity, and an amplitude associated with the altered time-varying intensity; and
determine a measurement of a characteristic of the powder bed in accordance with the optical property by calculating an absorption coefficient in accordance with the selected member.

23. The system of claim 17, wherein the processor is operable to determine a measurement of a characteristic of the powder bed in accordance with the optical property by calculating an isotropic scattering coefficient in accordance with the selected member.

24. The system of claim 17, wherein:
the source is operable to illuminate a location of the powder bed with a light by illuminating the location of the powder bed with a periodic, time-varying modulated light; and the processor is operable to:
measure the altered time-varying intensity of the light to generate a time-dependent signal by determining a member selected from a group consisting of a phase shift, an average of the time varying intensity, and an amplitude associated with the altered time-varying intensity; and
determine a measurement of a characteristic of the powder bed in accordance with the optical property by calculating an isotropic scattering coefficient in accordance with the selected member.

25. The system of claim 17, wherein the processor is operable to determine a uniformity associated with the powder bed in accordance with the variance and the sampled volume by:
determining a variance threshold for a perfectly mixed powder bed according to the sampled volume and a target concentration;
evaluating whether the variance satisfies the variance threshold for the perfectly mixed powder bed; and
determining the uniformity associated with the powder bed in accordance with the evaluation.

26. The system of claim 17, wherein:
the source is operable to illuminate a location of the powder bed with a light by using a plurality of wavelength sources, each wavelength source modulated with an identifiable intensity modulation;
the detector is operable to detect the light received from the powder bed by detecting the light having a plurality of modulation frequencies at a detector; and
the processor is operable to:
measure the altered time-varying intensity of the light to generate a time-dependent signal by separating the modulation frequencies and generating a time dependant signal for each modulation frequency and each wavelength; and
determine a measurement of a characteristic of the powder bed in accordance with the optical property by determining a characteristic.

27. The system of claim 17, wherein:
the source is operable to illuminate a location of the powder bed with a light by illuminating the location with a light having a plurality of modulation frequencies; and
the detector is operable to detect the light received from the powder bed by detecting the light having the plurality of modulation frequencies, the light at each modulation frequency describing a measurement of the characteristic.

28. The system of claim 17, further comprising a plurality of sources comprising the source, each source operable to generate light at a different modulation frequency, each source associated with a different source-detector distance, the sources generating light having a plurality of modulation frequencies, wherein the detector is operable to detect the light having the plurality of modulation frequencies using a detector, the light at each frequency describing a measurement of the characteristic associated with a source-detector distance.

29. The system of claim 17, further comprising a probe comprising the source and the detector, the probe operable to interface with the powder.

30. The system of claim 29, wherein the probe comprises a disposable probe.

31. The system of claim 17, further comprising a receptacle coupled to the source and the detector, the powder bed disposed within the receptacle, wherein:
the receptacle is operable to move the powder bed with respect to a location of the powder bed; and
the source is operable to illuminate the location of the powder bed.

32. The system of claim 17, wherein the characteristic of the powder bed comprises an element selected from a group consisting of particle packing density and particle shape.

* * * * *